(12) United States Patent
Zhang et al.

(10) Patent No.: US 12,274,817 B2
(45) Date of Patent: Apr. 15, 2025

(54) AIR DISINFECTION TROFFER

(71) Applicant: BOLB INC., Livermore, CA (US)

(72) Inventors: Jianping Zhang, Livermore, CA (US); Huazhong Deng, Livermore, CA (US); Ling Zhou, Livermore, CA (US); Ying Gao, Livermore, CA (US)

(73) Assignee: BOLB INC., Livermore, CA (US)

( * ) Notice: Subject to any disclaimer, the term of this patent is extended or adjusted under 35 U.S.C. 154(b) by 347 days.

(21) Appl. No.: 18/091,276

(22) Filed: Dec. 29, 2022

(65) Prior Publication Data

US 2024/0139367 A1 May 2, 2024

(30) Foreign Application Priority Data

Oct. 26, 2022 (CN) .......................... 202211316706.X

(51) Int. Cl.
*A61L 9/20* (2006.01)

(52) U.S. Cl.
CPC .............. *A61L 9/20* (2013.01); *A61L 2209/14* (2013.01); *A61L 2209/15* (2013.01)

(58) Field of Classification Search
None
See application file for complete search history.

(56) References Cited

U.S. PATENT DOCUMENTS

| 8,048,370 | B1 * | 11/2011 | Barnes | A61L 9/20 422/4 |
| 2023/0088479 | A1 * | 3/2023 | Palabrica | B60H 3/0078 422/186.3 |
| 2024/0042074 | A1 * | 2/2024 | Wang | F21V 33/0064 |

FOREIGN PATENT DOCUMENTS

| CN | 108195000 A | * | 6/2018 | |
| CN | 110087694 A | * | 8/2019 | ............ A61L 9/20 |
| DE | 202019107139 U1 | * | 3/2020 | ............ A61L 9/015 |
| DE | 202020104056 U1 | * | 11/2020 | |
| KR | 200493245 Y1 | * | 3/2021 | |
| WO | WO-2023023478 A1 | * | 2/2023 | ............ A61L 9/20 |

* cited by examiner

Primary Examiner — Andrew Smyth
(74) Attorney, Agent, or Firm — J.C. PATENTS

(57) ABSTRACT

The present application discloses a ceiling-mount air disinfector, i.e., an air disinfection troffer, including: a housing; a first air outlet and a first air inlet respectively near two opposing ends of a side of the housing; a filter covering the first air inlet; a cross flow fan located near the first air outlet, and an air disinfection apparatus disposed in the housing including an ultraviolet disinfection mechanism and an air rectifying chamber, said air rectifying chamber including a plurality of air ducts configured in parallel. In operation, ultraviolet light and air flow are introduced into the air ducts, traveling toward each other along a long side of the air ducts so that maximized air-light interaction time is achieved for the best disinfection efficacy.

16 Claims, 8 Drawing Sheets

AIR DISINFECTION TROFFER

CROSS-REFERENCE TO RELATED APPLICATION

The application claims the benefit to Chinese application No. 202211316706.X, filed on Oct. 26, 2022, the content of which is hereby incorporated by reference in its entirety.

TECHNICAL FIELD

The present disclosure relates to air disinfection and, in particular, to a troffer type air disinfector suitable for ceiling-mounting.

BACKGROUND OF THE RELATED ART

Air purifiers on the present market are mainly used for eliminating odor, methanol, particulate dust and suspended matters. They are incapable of eliminating airborne microorganisms such as bacteria and viruses. Moreover, most air purifiers on the market are made of a filtration material with small meshes, hence are intrinsically of high air flow resistance. This means that they are noisy, energy inefficient, and in need of frequent replacement of the costly filter element. More often, previous air purifiers are floor standing units, occupying a good deal of the precious indoor space.

SUMMARY

The present disclosure aims at solving at least one of the above-mentioned technical problems in the prior art to a certain extent. For this purpose, an embodiment of the present disclosure provides an air disinfection troffer, i.e., an air disinfector suitable for ceiling-mounting. The air disinfection troffer according to this disclosure can be mounted into an indoor ceiling to save indoor space, and is quite and energy efficient for high efficiency air disinfection.

The air disinfection troffer according to an embodiment of the present disclosure includes a housing, wherein a first air outlet and a first air inlet are provided on a side of the housing near two ends of the side of the housing; a filtration apparatus covering the first air inlet; an air disinfection apparatus disposed in the housing including an ultraviolet disinfection mechanism and an air rectifying chamber, said air rectifying chamber including a plurality of air ducts configured in parallel, wherein each of the air ducts includes a second air inlet and a second air outlet, wherein each of the second air inlet directly facing the first air inlet, and the ultraviolet disinfection mechanism being disposed at the vicinity of each of the second air outlets of the air ducts, wherein the ultraviolet disinfection mechanism emits ultraviolet light into the air ducts; and a fan of a third inlet and a third outlet mounted in the housing with the third outlet facing directly at the first air outlet, and the ultraviolet disinfection mechanism being located between third inlet of the fan and the second air outlets.

The geometry of the housing of the air disinfection troffer is optionally to be of a rectangular prism, meaning its length L, width W and height H are in a relation of L≥W>H. In one embodiment, L=W=24 inches, and H=4 inches; In another embodiment, L=48 inches, W=24 inches, and H=4 inches. Here, the selection of the dimensions is to fit into the ceiling grid style in the United States of America. L, W, H can be selected in other dimensions to fit into other styles of ceiling grid.

For the air disinfection troffer according to an embodiment of the present disclosure, the ultraviolet disinfection mechanism includes ultraviolet light sources; each of the second air outlets is provided with a ultraviolet light source; and an irradiation direction of the ultraviolet light source is parallel to an extension direction of the air duct, wherein a distance from the ultraviolet light source to the second air outlet ranges from 20 mm to 40 mm.

The air duct extension direction is optionally parallel to a length direction of the housing.

For the air disinfection troffer according to an embodiment of the present disclosure, the ultraviolet light source includes an ultraviolet light-emitting diode (LED) module, a fixing frame and a set of reflectors; each LED of the ultraviolet LED module is enclosed by a reflector; and the reflectors are fixed to the LED module via the fixing frame.

For the air disinfection troffer according to an embodiment of the present disclosure, the ultraviolet light source further includes at least a light transmitting window and a heat radiator; the fixing frame is provided with at least a fixing housing for enclosing and holding the reflector; an end portion of the fixing housing is formed with a washer cap; the light transmitting window is pressed against an end of the reflector by the washer cap of the fixing housing; and the heat radiator is fixed to a side of the ultraviolet LED module facing the fan.

For the air disinfection troffer according to an embodiment of the present disclosure, an opening direction of the second air outlet is parallel to the extension direction of the air duct; and an opening direction of the second air inlet is parallel to the extension direction of the air duct.

For the air disinfection troffer according to an embodiment of the present disclosure, a surface of the air duct is reflective to ultraviolet light and made of aluminum with surface finish in one of the following approaches: mirror polishing, vacuum deposition, electroplating, and Teflon spraying.

For the air disinfection troffer according to an embodiment of the present disclosure, a cross-sectional area of the second air inlets is smaller than a cross-sectional area of the first air inlet; and with the filtration apparatus covering the first air inlet, the housing, the filtration apparatus and the air rectifying chamber form a transition chamber.

For the air disinfection troffer according to an embodiment of the present disclosure, the filtration apparatus includes an air inlet net, a preliminary filter, a first fixing frame and a second fixing frame; the first fixing frame is disposed around the first air inlet; the first fixing frame is covered by the air inlet net; and the preliminary filter is laid on grid holes of the air inlet net and is pressed against the air inlet net via the second fixing frame.

For the air disinfection troffer according to an embodiment of the present disclosure, the housing further includes an arc-shaped air guide cover; and the air drawn by the fan can be guided to the first air outlet by the air guide cover.

For the air disinfection troffer according to an embodiment of the present disclosure, the fan is a cross-flow fan; and an indicator light for checking work status can be disposed on a surface of the housing.

The air disinfection troffer according to an embodiment includes a housing having a first air outlet and a first air inlet; an air disinfection apparatus disposed in the housing, air the disinfection apparatus includes one or more ultraviolet light sources and one or more air ducts arranged in parallel with each other, wherein each of the air ducts includes a second air inlet and a second air outlet, the second air inlet is in fluid communication with the first air inlet, and each of the one or more ultraviolet light sources faces the second air outlet of a corresponding air duct and emits ultraviolet light into the air duct along a longitudinal axis of the air duct; and a fan mounted in the housing with its exit side facing the first air outlet and its entrance side facing a backside of the ultraviolet light sources, and the ultraviolet light sources being located between the fan and the second air outlet.

The air disinfection troffer according to an embodiment includes 4-8 of the ultraviolet light sources and 4-8 of the air ducts, wherein the housing is of a cuboid shape with a length L, a width W and a height H, the air ducts have a rectangular or square cross-section, a length of each of the air ducts is in the range of 60%-90% of the length L, a height of each of the air ducts is in the range of 88%-98% of the height H.

The air disinfection troffer according to an embodiment, wherein the second air inlet is an opening on a sidewall, that faces the first inlet, of the air ducts at an air-intake end, and a size of the opening is equal to or larger than a cross-sectional area of the air duct.

Based on the above-mentioned technical solutions, the embodiments of the present disclosure at least have the following beneficial effects: in the above-mentioned technical solutions, during use, the fan runs to enable an air flow to enter from the first air inlet, particulate dust and parts of bacteria in the air flow entering from the first air inlet are filtered by the filtration apparatus, and thus, preliminary purification of the air flow is achieved; then, the preliminarily filtered air flow is guided and rectified by the air rectifying chamber, and the plurality of air ducts disposed in parallel in the air rectifying chamber divide the incoming air flow into a plurality of smaller air flows, which can be more uniformly disinfected within each air duct as the air ducts also guide the ultraviolet light propagation once the light enters the air ducts through the second air outlets; moreover, due to the arrangement of the plurality of air ducts, the flow rate of the air flow can be more uniform, so is the irradiation dose of the ultraviolet light emitted by the ultraviolet light source and received by the microbes in the air flow. As the air flow and ultraviolet light propagation in the air ducts proceed along the same axis but opposite directions, this maximizes the air and ultraviolet light interaction time hence maximizes the ultraviolet dose delivery to the air flow. Compared to the prior art air purifiers using high efficiency particulate air (HEPA) filters, the air disinfection troffer according to this disclosure only utilizes a preliminary filter to block coarse particles in the air but uses ultraviolet light propagating in parallel with the air flow to maximize ultraviolet dosage to the air. The air disinfection troffer according to this disclosure is hence more disinfection effective and energy efficient. Further, the rectangular prism shape design of the air disinfection troffer allows for adoption of a cross flow fan, which is inherently quieter and more energy efficient than other types of fans. And the fan is not disposed in the vicinity of the filtration apparatus, so that the air flow resistance is effectively lowered, and the capability of the fan extracting the air flow can be greatly improved. The air disinfection troffer according to this disclosure is simple in structure, convenient to maintain and space saving.

BRIEF DESCRIPTION OF DRAWINGS

The present disclosure will be further described below in conjunction with the accompanying drawings and embodiments.

DETAILED DESCRIPTION OF THE EMBODIMENTS

Figure 1:
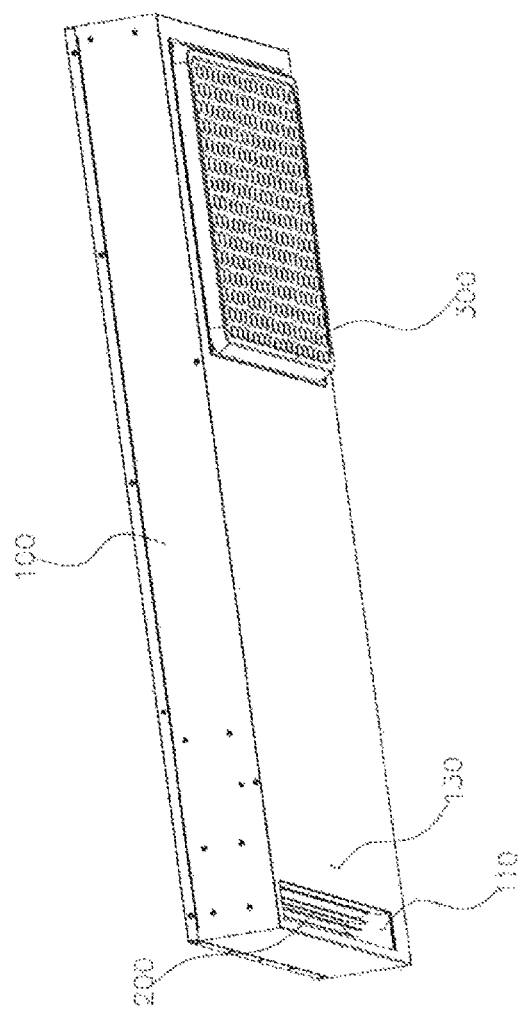
FIG. 1 is a perspective view of an air disinfection troffer according to the present disclosure.
Figure 2:
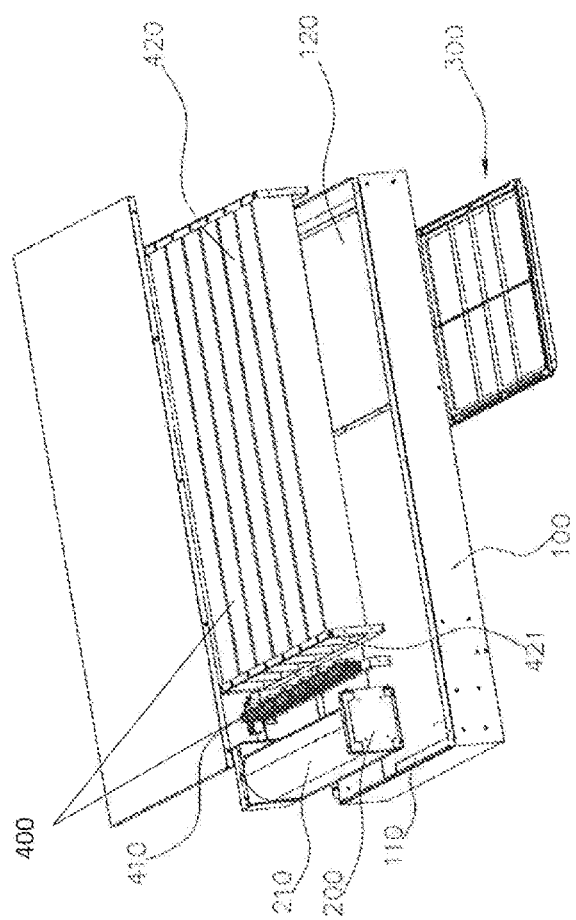
FIG. 2 is an exploded view of an air disinfection troffer according to the present disclosure.

The specific embodiments of the present disclosure will be described in detail herein, and preferred embodiments of the present disclosure will be shown in the accompanying drawings which play a role in replenishing the description for the language part in the specification with graphs to make people intuitively and vividly understand each of technical features and entire technical solutions of the present disclosure, but should not be understood as limiting on the protection scope of the claimed invention.

In the description of the present disclosure, it should be understood that descriptions for directions are involved, for example, directional or positional relationships indicated by upper, lower, front, rear, left, right, etc. are directional or positional relationships based on the accompanying drawings, are merely intended to facilitate describing the present disclosure and simplifying the description, rather than to indicate or imply that the appointed apparatus or element has to be located in a specific direction or structured and operated in the specific direction so as not to be understood as limiting on the claimed invention.

In the description of the present disclosure, "a plurality of" means two or more, "greater than", "smaller than", "exceeding", etc. are understood as exclusion of this number, and "above", "below", "within", etc. are understood as inclusion of this number. If there are descriptions for first and second, they are only for the purpose of distinguishing the technical features, and cannot be understood as indicating or implying the relative importance or implicitly indicating the number of indicated technical features or implicitly indicating the precedence relationship among the indicated technical features.

In the description of the present disclosure, words such as "disposed", "mounted", "connected", etc. should be understood in a broad sense unless otherwise defined. The skilled in the art can reasonably determine the specific meanings of the above words in the present disclosure in conjunction with specific contents of the technical solutions.

With reference to FIG. 1 to FIG. 5, an air disinfection troffer according to an embodiment of the present disclosure includes a housing 100, a filter 300, an air disinfection apparatus 400 and a fan 200.

The housing 100 can be a sealed hollow box of a shape suitable for ceiling mounting. In an embodiment, the housing 100 has a shape of a rectangular prism with a length L, a width W and a height H, where L≥W>H. In one embodiment, L=W=24 inches, and H=4 inches, and the length and height of each of the air ducts is in the range of 14-21 and 3.5-3.9 inch, respectively; In another embodiment, L=48 inches, W=24 inches, and H=4 inches, and the length and height of each of the air ducts is in the range of 29-43 and 3.5-3.9 inch, respectively. Here, the selection of the dimensions is to fit into the ceiling grid style in the United States of America. The length, width, and height (i.e., L, W, and H) as well as the shape of housing 100 can be selected in other dimensions to fit into other styles of the ceiling grid.

Figure 3:
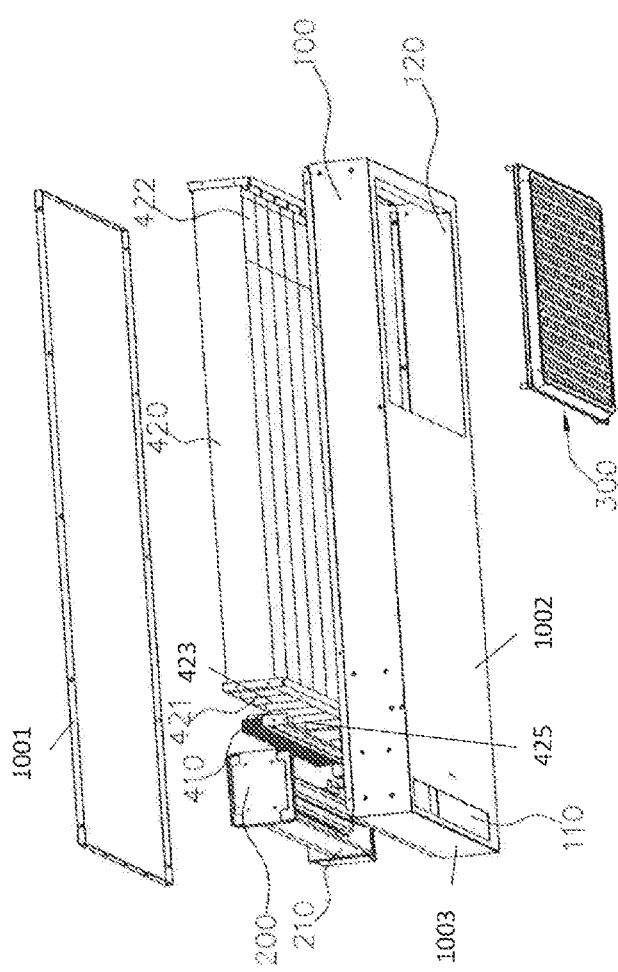
FIG. 3 is an exploded view of an air disinfection troffer according to the present disclosure.

According to an embodiment, the housing 100 has a top plate 1001 such as a flat top plate, a bottom plate 1002 such as a flat bottom plate, and a side wall 1003 (such as four flat side walls) connected to the top plate 1001 and the bottom plate 1002 at the upper edge and the lower edge of the side wall 1003, respectively, as shown in FIG. 3. When the air disinfection troffer is mounted into the ceiling of a room, the top plate 1001 of the housing 100 may be upwardly immersed in the drop ceiling, and the bottom plate 1002 of the housing 100 may be exposed to the room. In the vicinities of two opposing ends of the bottom plate 1002 of the housing 100 there are provided with a first air outlet 110 and a first air inlet 120, respectively. The filter 300 covers the first air inlet 120 and is configured to perform preliminary filtration to an air flow entered from the first air inlet 120.

The air disinfection apparatus 400 is disposed in the housing 100, including at least an ultraviolet light source 410 and an air rectifying chamber 420. The air rectifying chamber 420 includes a plurality of air ducts 421 disposed in parallel with each other, optionally running along a length direction of the housing 100. In the embodiment shown in FIG. 2, there are six air ducts 421 in total; while in other embodiments, there may be only one air duct 421, or three to ten air ducts 421. The number of air ducts 421 depending on application can vary and is not specifically limited herein. Moreover, as seen in FIG. 3, there are a few (six shown) second air inlets 422, all facing directly to the first air inlet 120 and each respectively corresponding to an air duct 421 (i.e., being the air inlet of a corresponding air duct 421). Air intake through the first air inlet 120 thus is received by the second air inlets 422, divided into several air flows and rectified by the air ducts 421. The at least one (six shown in FIG. 5) ultraviolet light source 410 is disposed at the second air outlets 423 of the air ducts 421, wherein ultraviolet light emitted by the ultraviolet light source 410 enters into and propagates along a corresponding air duct 421, respectively, while the air flows received from the second air inlets 422 flow against the propagating ultraviolet light in the air ducts 421, thus maintain a maximized contact time with ultraviolet light, receiving a maximized ultraviolet light dose, hence a maximized disinfection effect. To reduce the ultraviolet light loss during the propagation in the air ducts 421, two arrangements can be made. First, a majority of the ultraviolet light optionally enters into the air ducts 421 with small impinge angles to reduce the reflection times on the inner surface of the air ducts 421. In an ideal case, the impinge angle can be zero, meaning the ultraviolet light is collimated and in parallel with the longitudinal axis of the air ducts 421. In practice, one can focus the ultraviolet light from the ultraviolet light source 410 to make a majority (i.e., more than 50%) of the ultraviolet light enter into the air ducts 421 with impinge angles less than 45, or, 30, or 20 degrees. Second, the inner surface of the air ducts 421 can be made ultraviolet reflective, for example, to be of ultraviolet reflectance better than 50%, 70%, 80%, or 90%.

There is a gap 425 between the ultraviolet light sources 410 and the second air outlets 423 (Shown in FIGS. 3 and 4), so that the air can exit from the air ducts 421 through the gap 425. The second air inlets 422 can be formed as an opening on the side wall of the air ducts 421.

The length of the air duct 421 can be in the range of 20-500 cm (about 7.88-197 inch) depending on the length of the housing 100. For example, when the length L of housing 100 is 4 feet (~122 cm), the length of the air duct 421 can be about 90 cm (about 35.46 inch). The number of air ducts 421 can be approximately determined by the width Wand height H of the housing 100, i.e., to be ~ W/H. This means that the air ducts 421 prefer to be of a square cross section, and the width of the air ducts 421 therefore approaches H but stays slightly less than H (as housing 100 has a top plate 1001 and a bottom plate 1002 of a certain thickness). For example, if the housing 100 is of width W=2 feet and height H=4 inches, then the number and width of air ducts 421 are 6 and ~10 cm (about 3.94 inch), respectively. Round and rectangular air ducts 421 may also be used in some other embodiments, but they are less desirable in terms of air flow resistance and dose delivery effectiveness. If the installation space allows for large H, large air ducts 421 can be applied, for better dose delivery effectiveness. The air duct 421 is optionally a straight duct with a uniform cross-section throughout its entire length.

The fan 200 is mounted in the housing 100 with its exit side facing the first air outlet 110 directly and its entrance side facing a backside of the ultraviolet light sources 410, which are located between the fan 200 and the second air outlets 423 of the air ducts 421, with a front side facing the air ducts 421 so that the ultraviolet light emitted by the light sources 410 can be aligned with and enter corresponding air ducts 421, respectively. Therefore, the air flow drawn from the first air inlet 120 into the air disinfection apparatus 400 by the fan 200 can be disinfected. In the embodiment shown in FIGS. 1-3, the fan 200 is disposed at the first air outlet 110 of the housing 100 and is not close to the filter 300. This arrangement can effectively reduce the air flow resistance experienced by the fan 200, making the fan 200 quieter and more energy efficient. Further, the rectangular prism shape design of the air disinfection troffer allows for adoption of a cross flow fan, which is inherently quieter and more energy efficient than other types of fans. Moreover, the fan 200 is disposed downstream of the ultraviolet light sources 410 in terms of the air flow and thus is capable of extracting heat generated by the ultraviolet light sources 410 while extracting the air flow. This can maintain a suitable temperature of the ultraviolet light sources 410 so that their efficiency and lifetime can be improved.

In operation, the fan 200 is turned on to enable an air flow to enter from the first air inlet 120; most particulate dust and a part of microorganisms in the air flow entering from the first air inlet 120 can be filtered out by the filter 300, thus a preliminary filtration of the air flow is achieved; then, the filtered air flow is received by the second air inlets 422 and divided into several air flows into, and rectified by, the air ducts 421, which are arranged in parallel configuration in the air rectifying chamber 420. The arrangement of multiple air ducts 421 in parallel makes the air disinfection more uniform as the air ducts 421 also guide the ultraviolet light propagation once the ultraviolet light enters the air ducts 421 through the second air outlets 421; moreover, due to the arrangement of the plurality of air ducts, the flow rate of the air flow can be more uniform, so is the irradiation dose of the ultraviolet light emitted by the ultraviolet light source and received by the microbes in the air flow. As the air flow and ultraviolet light propagation in the air ducts 421 proceed in parallel and along the same axis but opposite directions, this maximizes the air and ultraviolet light interaction time, hence maximizes the ultraviolet dose delivery to the air flow. Compared to the prior art air purifiers using high efficiency particulate air (HEPA) filters, the air disinfection troffer according to this disclosure not only utilizes a preliminary filter (i.e., a filter of Minimum Efficiency Reporting Value (MERV) less than 10) to block coarse particles in the air, also uses ultraviolet light propagating in parallel with the air flow to maximize ultraviolet dosage to the air. The air disinfection troffer according to this disclosure is hence more disinfection effective and energy efficient. Further, the rectangular prism shape design of the air disinfection troffer allows for adoption of a cross flow fan, which is inherently quieter and more energy efficient than other types of fans. And the fan 200 is not disposed in the vicinity of the filter 300, so that the air flow resistance is effectively lowered, and the capability of the fan extracting the air flow can be greatly improved. The air disinfection troffer according to this disclosure is simple in structure, convenient to maintain and space saving.

Figure 4:
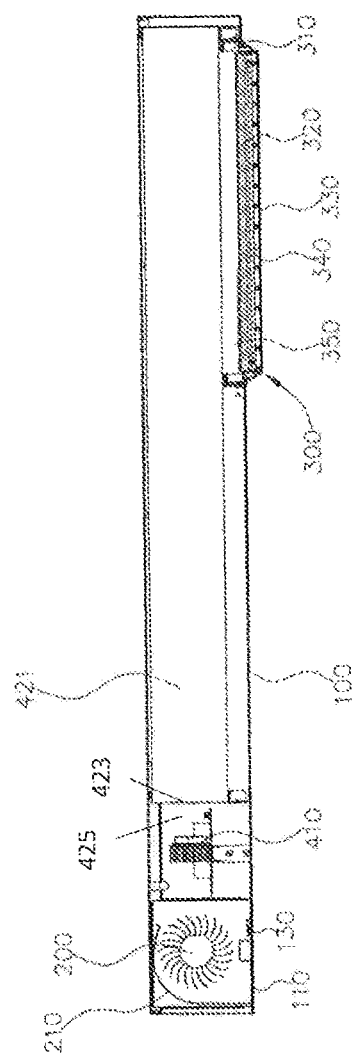
FIG. 4 is a side cross-sectional view of an air disinfection troffer according to the present disclosure.
Figure 5:
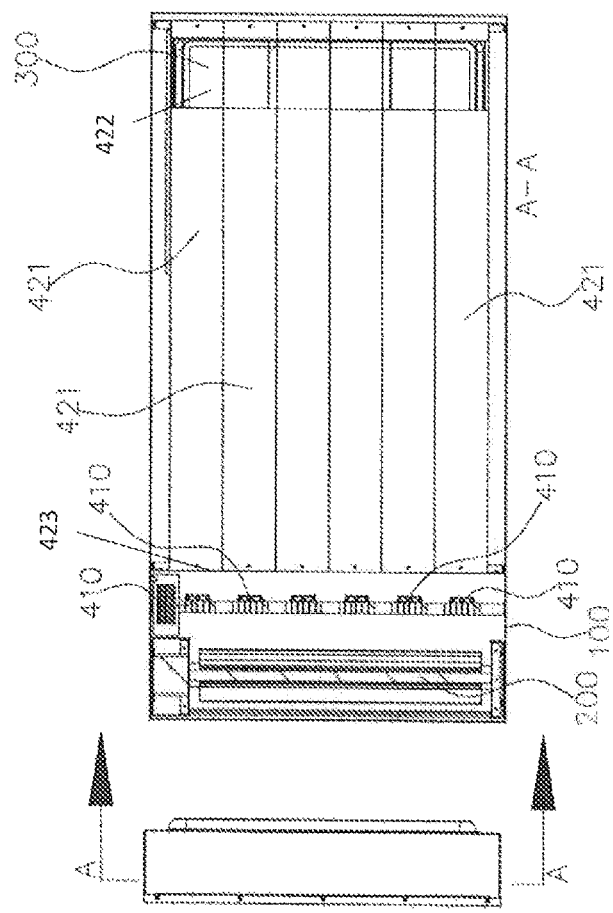
FIG. 5 is a structural sectional view in direction A-A of an air disinfection troffer according to the present disclosure.

As shown in FIG. 5, the air disinfection apparatus 400 includes at least one (six shown) ultraviolet light sources 410, each of the second air outlets 423 (six shown) is provided and aligned with one ultraviolet light source 410, and the irradiation direction of the ultraviolet light sources 410 is in parallel to the longitudinal axis of the air ducts 421, respectively. In an embodiment, each ultraviolet light source 410 directly faces the opening of the second air outlet 423 of a corresponding air duct 421 and is aligned with the longitudinal axis of the air duct 421, so that it emits ultraviolet light into the air duct 421 along its longitudinal axis. The opening of the second air outlet 423 may have a dimension the same as the cross-section of the air duct 421. On the other hand, the second air inlet 422 can be formed by removing a portion of the sidewall (that faces the first inlet 120) of the air ducts 421 at the air-intake end, or can be an opening on the sidewall (that faces the first inlet 120) of the air ducts 421 at the air-intake end, as show in FIG. 4. Optionally, the size of the opening is equal to or larger than the cross-sectional area of the air duct 421. In another embodiment, the air ducts 421 do not extend the entire length of the air rectifying chamber 420, leaving an empty chamber at the air-intake end of the air rectifying chamber 420 to form a common second air inlet 422 shared by all of the air ducts 421. This arrangement improves the air disinfection efficiency, ensures an evenly distributed irradiation dose of the ultraviolet light to the air flows in all air duct 421. The ultraviolet irradiation or propagation direction of the ultraviolet light sources 410 being in parallel to the longitudinal axis of the air duct 421 maximizes the air-light contact time, therefore maximizes the ultraviolet light dose to the air. The small light impinge angles into the air ducts 421 minimize the ultraviolet light loss during propagation in the air ducts 421. That the ultraviolet light being irradiated from the second air outlets 423 to the second air inlets 422 of the air ducts 421 also benefits the irradiation time of the ultraviolet light received by the air flows, improving the disinfection efficiency, feasibly up to more than 99%. Optionally, a distance from an ultraviolet light sources 410 to a corresponding second air outlet 423 (i.e., the gap between a front surface (such as the outer surface of a light transmitting window 415) of an ultraviolet light source 410 and a corresponding second air outlet 423 (such as the outermost cross-sectional surface of the second air outlet 423) ranges from 20 mm to 40 mm (about 0.788 to 1.576 inch), to ensure a small and proper air flow resistance; too small distance will cause high flow resistance; too large distance may cause less ultraviolet light coupling into the air ducts 421.

Figure 6:
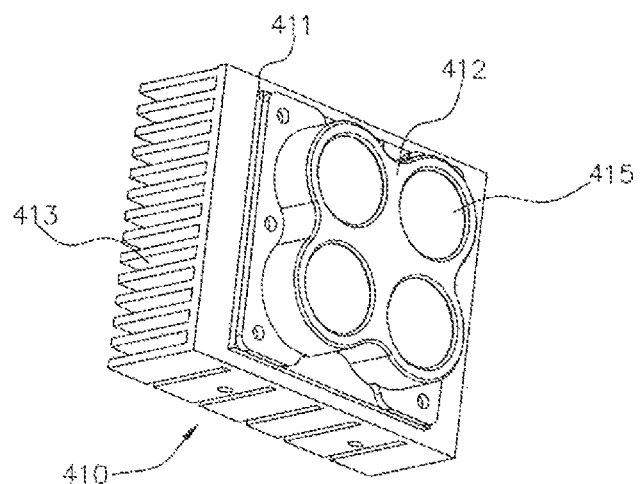
FIG. 6 is a perspective view of an ultraviolet light source according to an embodiment of the present disclosure.
Figure 7:
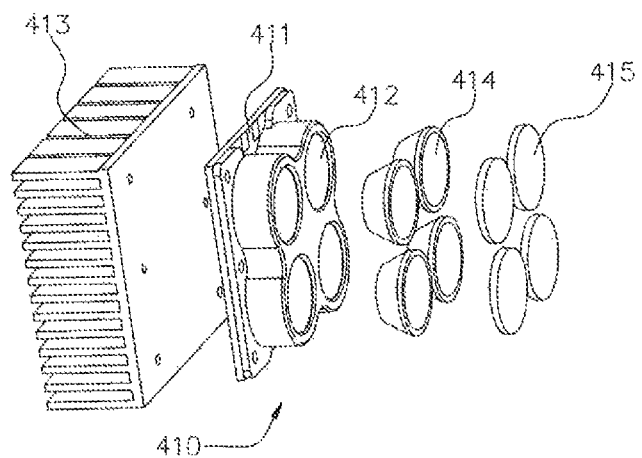
FIG. 7 is an exploded view of an ultraviolet light source according to an embodiment of the present disclosure.
Figure 8:
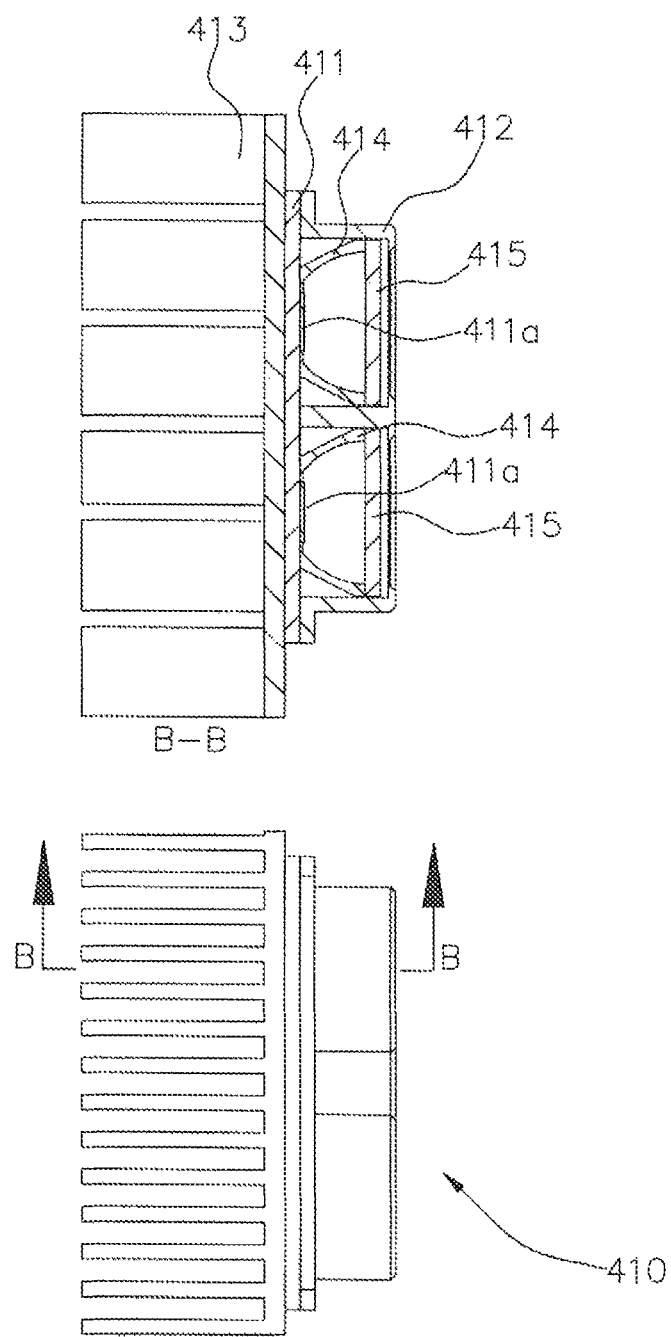
FIG. 8 is a structural sectional view in direction B-B of an ultraviolet light source of FIG. 6 according to an embodiment of the present disclosure.

Further, as shown in FIGS. 6-8, the ultraviolet light source 410 includes an ultraviolet LED module 411, a fixing frame 412 and reflectors 414. The LED module 411 may contain several ultraviolet LEDs 411a, and each of the ultraviolet LED 411a is enclosed by a reflector 414, and the reflectors 414 are fixed to the LED module 411 via the fixing frame 412. A light source frame for support the ultraviolet light sources 410 can be used. And the ultraviolet light sources 410 are disposed in the housing 100, so that each irradiating into one of the air ducts 421. The LED module 411 is provided with a plurality of high-power ultraviolet LEDs 411a; in the embodiment shown in FIGS. 6-7, there are four ultraviolet LEDs 411a for an LED module 411. The wavelength of these LEDs are optionally to be shorter than 285 nm so that they are deep ultraviolet LEDs. The number of ultraviolet LEDs can vary based on the required irradiation dose. High power ultraviolet light is provided by a plurality of high-power ultraviolet LEDs 411a so that the disinfection efficiency can be sufficient. Moreover, each of the LEDs 411a is enclosed by a reflector 414 to focus and shape the emission angles of impingement, so that to reduce ultraviolet light loss during the propagation in the air ducts 421.

Specifically, as shown in FIG. 8, the ultraviolet light source 410 further includes a light transmitting window 415 and a heat radiator 413. The fixing frame 412 is provided with a number of fixing housings to hold the reflectors 414. The fixing housings are used to restrict and pin down the positions of the reflectors 414; an end portion of the fixing housing is formed with a washer cap, a cap extending from an outer edge of an end portion of the fixing housing to the central axis of the fixing housing; the light transmitting window 415 is pressed against an end of the reflector 414 by the washer cap of the fixing housing. In the present embodiment, the light transmitting window 415 is made of quartz, or ultraviolet grade glass; and by disposing the light transmitting windows 415, dusts not filtered by the filter 300 can be prevented from accumulating on the LEDs 411a and the reflectors 414. The light transmitting windows 415 are easy to clean during maintenance even if dusts accumulate thereon. Further, a heat radiator 413 is fixed to the other side of the LED module 411, facing the fan 200; and by disposing the heat radiator 413, heat generated by the LED module 411 can be effectively radiated to the disinfected air.

As shown in FIG. 4 and FIG. 5, the opening direction of the second air outlet 423 is in parallel with the longitudinal axis of the air duct 421, so is the opening direction of the second air inlet 422 [note that the second inlets 422 also face the first inlet 120]. This arrangement allows the preliminary filtered air flow to enter the air ducts 421 with small air flow resistance. And the air ducts 421 are straight, facilitating air flowing and ultraviolet light propagating. The inner surface of the air ducts 421 can be made ultraviolet reflective, with a reflectance larger than 50%, 70%, 80%, or 90%, such as 50% to 99%. And the ultraviolet light reflection optionally is a specular reflection, to maintain a propagation forward of the ultraviolet light in the air ducts 421. The ultraviolet light impinging into the second air outlets 423 of the air ducts 421 thus propagates in the air ducts 421, and intercepts the air flows coming from the second air inlets 422. The ultraviolet irradiation or propagation direction of the ultraviolet light sources 410 being in parallel to the longitudinal axis of the air duct 421 maximizes the air-light contact time, therefore maximizes the ultraviolet light dose to the air. The time that the air flows are exposed to the ultraviolet light is greatly prolonged, that is, the time that the microbes in the air are exposed to the ultraviolet light is prolonged, and thus the purpose of high-effectiveness disinfection is achieved. It needs to be noted that, in the present embodiment, the air ducts 421 may be made of aluminum (Al), as Al is of good ultraviolet reflectance depending on the surface finish. To this end, the surface of the Al air ducts 421 can be treated with mirror polishing, so that it has the best capacity of reflecting the ultraviolet light. The inner surface of air ducts 421 can also be made of vacuum deposition, electroplating Al. In other embodiments, the inner surface of the air ducts 421 can also be sprayed with Teflon, so that it can reflect the ultraviolet light. The air ducts 421 can also be made of other materials such as stainless steel, plastics, et al, as long as the surface finish is ultraviolet reflective.

In some embodiments, as shown in FIG. 3 and FIG. 4, the openings of the second air inlets 422 are smaller than the opening of the first air inlet 120. With the filter 300 covering the first air inlet 120, a transition chamber 350 is formed between the filter 300 and the second air inlets 422 of the air rectifying chamber 420. The transition chamber 350 is sealed against the rest portion of the housing 100, so that the air entered from the first air inlet 120 can only exit the housing 100 sequentially via the second air inlets 422, the air ducts 421, the second air outlets 423 and the first air outlet 110. That the openings of the second air inlets 422 being smaller than the opening of the first air inlet 120 means that the air filtration area of the filter 300 is greater than the openings of the second air inlets 422. This arrangement can reduce air flow resistance and improve filtration effect. And due to the formation of the transition chamber 350, there is a gap between the filter 300 and the air rectifying chamber 420, so that the air filtration volume of the filter 300 can be further increased, and the air flow resistance of the filter 300 to the air flow can be lowered.

Figure 9:
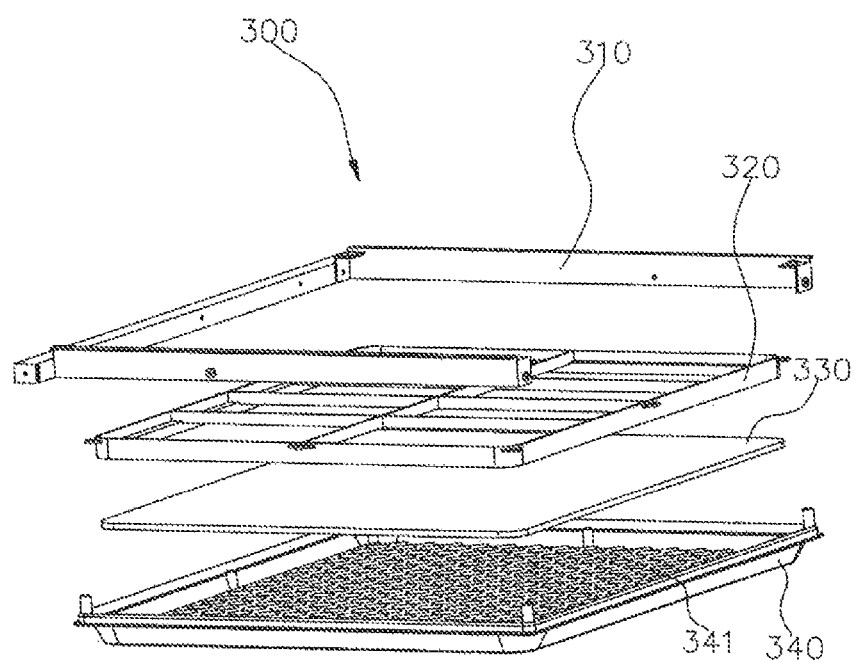
FIG. 9 is an exploded view of a filter according to an embodiment of the present disclosure.

Specifically, as shown in FIG. 9, in one embodiment, the filter 300 includes an air inlet net 340, a preliminary filter 330, a first fixing frame 310 and a second fixing frame 320. The first fixing frame 310 is disposed around the first air inlet 120, and it is covered by the air inlet net 340. The preliminary filter 330 is laid on grid holes 341 of the air inlet net 340 and is pressed against the air inlet net 340 via the second fixing frame 320. By using the preliminary filter 330, particulate dusts can be effectively filtered, and the situation that overload dusts enter the air ducts 421 is avoided. The preliminary filter 330 can also effectively filter a part of the bacteria, while keeping the air flow resistance low without affecting the air input and the air output of the entire air disinfection troffer. The preliminary filter 330 can be regularly replaced and cleaned, so that the phenomenon that overmuch dusts and sundries are gathered to affect the passing of the air flow is avoided. Generally speaking, the filter 300 is not limited to the specific structure shown in FIG. 9, instead, the filter 300 can be any suitable filter or filter system known in the art.

In other embodiments, as shown in FIG. 4, the housing 100 is further internally provided with a guide cover 210 with an arc-shaped cross section, by which air drawn by the fan 200 is guided to the first air outlet 110. As shown the direction of the first air outlet 110 is perpendicular to the flow direction of the disinfected air flow drawn by the fan 200. The guide cover 210 therefore guides the disinfected air flow to the first air outlet 110, without generating turbulence so as to improve the disinfection effectiveness and energy efficiency of the whole system. The arc-shaped guide cover 210 can smoothly change the flow direction of the disinfected air flow drawn by the fan 200 and guide the air flow to the first air outlet 110, so that the disinfected air flow flows from the first air outlet 110 to the indoors.

In addition, the fan 200 in the present embodiment is preferably a cross-flow fan which has the advantages of small size, muting, high efficiency and high fan air volume as compared with a common axial-flow fan of other like products.

Moreover, the cross-flow fan is provided at a back side of the LED module 411 where the heat radiator 413 is provided, and can produce high-speed air flow to remove the heat from the heat radiator 413 of the LED module 411. Moreover, the air disinfection troffer provided by the present disclosure can be mounted on an indoor ceiling and space can be saved. Due to the use of the cross-flow fan, the air disinfection troffer according to the present disclosure is capable of treating air of high flowrates (e.g., more than 7 $m^3$/min), hence suitable for large room air disinfection. Further, an indicator light 130 for checking the work status can be disposed outside the housing 100; and a user can clearly know about the running status of the air disinfection troffer via the indicator light 130. In summary, it can be known that the air disinfection troffer provided by the present disclosure adopts high-power deep ultraviolet LEDs by which 99.99% of bacteria can be deactivated; and it only uses a preliminary filter so that a low air flow resistance and low noise level can be maintained even for large air flow rates. The quietness, high efficiency in large air flow treatment, and small form factor make the device suitable for ceiling mount to do room air disinfection.

The embodiments of the present disclosure have been described in detail above in conjunction with the accompanying drawings; however, the present disclosure is not limited to the above-mentioned embodiments. Those of ordinary skill in the art may also make various variations within the scope of their knowledge without departing from the intention of the present disclosure.

The invention claimed is:

1. An air disinfection troffer, comprising:
    a housing, wherein a first air outlet and a first air inlet are provided on a bottom plate of the housing near two ends of the bottom plate of the housing;
    a filter covering the first air inlet;
    an air disinfection apparatus disposed in the housing, comprising one or more ultraviolet light sources and an air rectifying chamber, the air rectifying chamber comprising two or more air ducts arranged in parallel with each other, wherein each of the air ducts includes a second air inlet and a second air outlet, the second air inlet faces the first air inlet, and each of the one or more ultraviolet light sources is disposed facing and aligned with the second air outlet of a corresponding air duct, wherein the one or more ultraviolet light sources emits ultraviolet light into the one or more air ducts, respectively; and
    a fan mounted in the housing with its exit side directly facing the first air outlet and its entrance side facing a backside of the ultraviolet light sources, and the ultraviolet light sources being located between the fan and the second air outlet.

2. The air disinfection troffer according to claim 1, wherein an irradiation direction of the ultraviolet light source (410) is parallel with a longitudinal axis of the air duct (421), a distance from the ultraviolet light source (410) to the second air outlet ranges from 0.8-1.6 inch.

3. The air disinfection troffer according to claim 1, wherein the ultraviolet light source (410) includes an ultraviolet light-emitting diode (LED) module (411), a fixing frame (412) and a set of reflectors (414); each ultraviolet LED (411a) of the ultraviolet LED module (411) is enclosed by a reflector (414); and the reflectors (414) are fixed to the LED module (411) via the fixing frame (412).

4. The air disinfection troffer according to claim 3, wherein the ultraviolet light source (410) further includes a light transmitting window (415) and a heat radiator (413); the fixing frame (412) is provided with a fixing housing for enclosing and holding the reflector (414); an end portion of the fixing housing is formed with a washer cap; the light transmitting window (415) is pressed against an end of the reflector (414) by the washer cap of the fixing housing; and the heat radiator (413) is fixed to a side of the ultraviolet LED module (411) facing the fan (200).

5. The air disinfection troffer according to claim 1, wherein an opening direction of the second air outlet is in parallel with a longitudinal axis of the air duct (421); and an opening direction of the second air inlet is in parallel with the longitudinal axis of the air duct (421).

6. The air disinfection troffer according to claim 5, wherein an inner surface of the air duct (421) is reflective to ultraviolet light and made of aluminum with one of the following surface finishes: mirror polishing, vacuum deposition, electroplating, and Teflon spraying.

7. The air disinfection troffer according to claim 1, wherein a total cross-sectional area of the second air inlets (422) is smaller than a cross-sectional area of the first air inlet (120); and a transition chamber (350) is formed between the filter (300) and the second air inlets (422) of the air rectifying chamber (420); the transition chamber is sealed against the rest portion of the housing (100), so that air entered from the first air inlet (120) can only exit the housing (100) sequentially via the second air inlets 422, the air ducts (421), the second air outlets (423) and the first air outlet (110).

8. The air disinfection troffer according to claim 7, wherein the filter (300) includes an air inlet net (340), a preliminary filter (330), a first fixing frame (310) and a second fixing frame (320); the first fixing frame (310) is disposed around the first air inlet (120); the first fixing frame (310) is covered by the air inlet net (340); and the preliminary filter (330) is laid on grid holes (341) of the air inlet net (340) and is pressed against the air inlet net (340) via the second fixing frame (320).

9. The air disinfection troffer according to claim 1, wherein the housing (100) further comprises an air guide cover of an arc-shaped cross section (210); and the air drawn by the fan (200) can be guided to the first air outlet (110) by the air guide cover (210).

10. The air disinfection troffer according to claim 1, wherein the fan (200) is a cross-flow fan; and an indicator light (130) for checking work status is disposed on an outer surface of the housing (100).

11. The air disinfection troffer according to claim 1, wherein the housing has a width W and a height H, each of the air ducts (421) has a length in the range of 8-200 inch and a cross-section of a square shape, an number of the air ducts (421) is to be ~W/H, and a width of each of the air ducts (421) equals to H minus a thickness of the top plate and a thickness of the bottom plate.

12. The air disinfection troffer according to claim 1, wherein the housing has a length L, a width W and a height H, and L=24 inch, W=24 inch and H=4 inch; a length and a height of each of the air ducts is in the range of 14-21 and 3.5-3.9 inch, respectively.

13. The air disinfection troffer according to claim 1, wherein the housing has a length L, a width W and a height H, and L=48 inch, W=24 inch and H=4 inch; a length and a height of each of the air ducts is in the range of 29-43 and 3.5-3.9 inch.

14. An air disinfection troffer, comprising:

a housing having a first air outlet and a first air inlet;

an air disinfection apparatus disposed in the housing, comprising one or more ultraviolet light sources and two or more air ducts arranged in parallel with each other, wherein each of the air ducts includes a second air inlet and a second air outlet, the second air inlet is in fluid communication with the first air inlet, and each of the one or more ultraviolet light sources faces the second air outlet of a corresponding air duct and emits ultraviolet light into the air duct along a longitudinal axis of the air duct; and a fan mounted in the housing with its exit side facing the first air outlet and its entrance side facing a backside of the ultraviolet light sources, and the ultraviolet light sources being located between the fan and the second air outlet.

15. The air disinfection troffer according to claim 14, comprising 4-8 of the ultraviolet light sources (410) and 4-8 of the air ducts (421), wherein the housing is of a cuboid shape with a length L, a width W and a height H, the air ducts have a rectangular or square cross-section, a length of each of the air ducts is in the range of 60%-90% of the length L, a height of each of the air ducts is in the range of 88%-98% of the height H.

16. The air disinfection troffer according to claim 14, wherein the second air inlet is an opening on a sidewall, that faces the first inlet, of the air ducts at an air-intake end, and a size of the opening is equal to or larger than a cross-sectional area of the air duct.

* * * * *